(12) United States Patent
Sanchez Gutierrez et al.

(10) Patent No.: US 11,649,513 B2
(45) Date of Patent: May 16, 2023

(54) KIT FOR DETECTING SILENT SEXUALLY TRANSMITTED DISEASES (SSTDS) IN A URINE SAMPLE

(71) Applicant: UNIVERSIDAD DE LA FRONTERA, Temuco (CL)

(72) Inventors: Raul Segundo Sanchez Gutierrez, Temuco (CL); Alejandra Pilar Andana Vargas, Temuco (CL); Carmen Gloria Ili Gangas, Temuco (CL); Doris Menzel Middelmann, Temuco (CL); Jaime Patricio Lopez Mendez, Temuco (CL); Juan Carlos Roa Strauch, Temuco (CL); Priscilla Solange Brebi Mieville, Temuco (CL)

(73) Assignee: UNIVERSIDAD DE LA FRONTERA, Temuco (CL)

( * ) Notice: Subject to any disclaimer, the term of this patent is extended or adjusted under 35 U.S.C. 154(b) by 623 days.

(21) Appl. No.: 16/487,697

(22) PCT Filed: Mar. 3, 2017

(86) PCT No.: PCT/IB2017/051265
§ 371 (c)(1),
(2) Date: Aug. 21, 2019

(87) PCT Pub. No.: WO2018/158618
PCT Pub. Date: Sep. 7, 2018

(65) Prior Publication Data
US 2019/0376150 A1 Dec. 12, 2019

(51) Int. Cl.
*C12Q 1/70* (2006.01)
*C12Q 1/689* (2018.01)
*C12Q 1/686* (2018.01)

(52) U.S. Cl.
CPC ............. *C12Q 1/705* (2013.01); *C12Q 1/689* (2013.01); *C12Q 1/708* (2013.01); *C12Q 1/686* (2013.01)

(58) Field of Classification Search
None
See application file for complete search history.

(56) References Cited

PUBLICATIONS

León et al. Rev Chilena Infectol 33(5):505-512. (Year: 2016).*

* cited by examiner

*Primary Examiner* — Samuel C Woolwine
(74) *Attorney, Agent, or Firm* — Lucas & Mercanti, LLP

(57) ABSTRACT

A diagnostic kit for simultaneously detecting at least seven silent sexually transmitted diseases (SSTDs) having a diagnostic strip which has detection zones with at least eight probes with SEQ ID NOs: 3, 6, 9, 12, 15, 18, 21, 24; at least 14 primers with SEQ ID NOs: 1, 2, 4, 5, 7, 8, 10, 11, 13, 14, 16, 17, 19, 20, 22, 23; an instruction manual; a nucleotide sequence set for simultaneously detecting at least seven silent sexually transmitted diseases (SSTDs); use of the kit to detect at least the following pathogens: Herpes Virus type 1, Herpes Virus type 2, *Chlamydia trachomatis*, *Ureaplasma urealitycum*, *Mycoplasma hominis*, *Mycoplasma genitalium*, and Human papillomavirus (HPV); a method for simultaneously detecting at least seven silent sexually transmitted diseases (SSTDs).

5 Claims, 2 Drawing Sheets

Specification includes a Sequence Listing.

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: PRIMER

<400> SEQUENCE: 1
tggccaagct gacggacatt t					21

<210> SEQ ID NO 2
<211> LENGTH: 21
<212> TYPE: DNA
<213> ORGANISM: Artificial Sequence

```
<220> FEATURE:
<223> OTHER INFORMATION: PRIMER

<400> SEQUENCE: 2
gagagcttga tcttgtcggt t                                              21

<210> SEQ ID NO 3
<211> LENGTH: 24
<212> TYPE: DNA
<213> ORGANISM: Artificial Sequence
<220> FEATURE:
<223> OTHER INFORMATION: PROBE

<400> SEQUENCE: 3
taaaggtgaa cggcatggtg agca                                           24

<210> SEQ ID NO 4
<211> LENGTH: 20
<212> TYPE: DNA
<213> ORGANISM: Artificial Sequence
<220> FEATURE:
<223> OTHER INFORMATION: PRIMER

<400> SEQUENCE: 4
tgtttctggg cagctgtatc                                                20

<210> SEQ ID NO 5
<211> LENGTH: 22
<212> TYPE: DNA
<213> ORGANISM: Artificial Sequence
<220> FEATURE:
<223> OTHER INFORMATION: PRIMER

<400> SEQUENCE: 5
ctatcgacgt tagggaaggc at                                             22

<210> SEQ ID NO 6
<211> LENGTH: 24
<212> TYPE: DNA
<213> ORGANISM: Artificial Sequence
<220> FEATURE:
<223> OTHER INFORMATION: PROBE

<400> SEQUENCE: 6
catagatgcc agcgccgata cagg                                           24

<210> SEQ ID NO 7
<211> LENGTH: 23
<212> TYPE: DNA
<213> ORGANISM: Artificial Sequence
<220> FEATURE:
<223> OTHER INFORMATION: PRIMER

<400> SEQUENCE: 7
tcaaggagtg gagtgtctgc gta                                            23

<210> SEQ ID NO 8
<211> LENGTH: 22
<212> TYPE: DNA
<213> ORGANISM: Artificial Sequence
<220> FEATURE:
<223> OTHER INFORMATION: PRIMER

<400> SEQUENCE: 8
tgtcgctccg atgcagatgt tt                                             22
```

```
<210> SEQ ID NO 9
<211> LENGTH: 24
<212> TYPE: DNA
<213> ORGANISM: Artificial Sequence
<220> FEATURE:
<223> OTHER INFORMATION: PROBE

<400> SEQUENCE: 9
atagggagtg tttctcgcca agct                                              24

<210> SEQ ID NO 10
<211> LENGTH: 24
<212> TYPE: DNA
<213> ORGANISM: Artificial Sequence
<220> FEATURE:
<223> OTHER INFORMATION: PRIMER

<400> SEQUENCE: 10
gcaggcgggt ttgtaagttt ggta                                              24

<210> SEQ ID NO 11
<211> LENGTH: 24
<212> TYPE: DNA
<213> ORGANISM: Artificial Sequence
<220> FEATURE:
<223> OTHER INFORMATION: PRIMER

<400> SEQUENCE: 11
agcctaagcg tcagtgatag tcca                                              24

<210> SEQ ID NO 12
<211> LENGTH: 23
<212> TYPE: DNA
<213> ORGANISM: Artificial Sequence
<220> FEATURE:
<223> OTHER INFORMATION: PROBE

<400> SEQUENCE: 12
ataggaagaa caccggtggc gaa                                               23

<210> SEQ ID NO 13
<211> LENGTH: 24
<212> TYPE: DNA
<213> ORGANISM: Artificial Sequence
<220> FEATURE:
<223> OTHER INFORMATION: PRIMER

<400> SEQUENCE: 13
tggagaatca ctgacgcagc taac                                              24

<210> SEQ ID NO 14
<211> LENGTH: 24
<212> TYPE: DNA
<213> ORGANISM: Artificial Sequence
<220> FEATURE:
<223> OTHER INFORMATION: PRIMER

<400> SEQUENCE: 14
tgcgaaggat gtcaagagtg ggta                                              24

<210> SEQ ID NO 15
<211> LENGTH: 24
<212> TYPE: DNA
<213> ORGANISM: Artificial Sequence
<220> FEATURE:
<223> OTHER INFORMATION: PROBE
```

```
<400> SEQUENCE: 15
ccgcctgagt agtatgctcg caag                                          24

<210> SEQ ID NO 16
<211> LENGTH: 23
<212> TYPE: DNA
<213> ORGANISM: Artificial Sequence
<220> FEATURE:
<223> OTHER INFORMATION: PRIMER

<400> SEQUENCE: 16
cgcaacgctc aggtgtctaa tgt                                           23

<210> SEQ ID NO 17
<211> LENGTH: 20
<212> TYPE: DNA
<213> ORGANISM: Artificial Sequence
<220> FEATURE:
<223> OTHER INFORMATION: PRIMER

<400> SEQUENCE: 17
agagcttggc gcattgctga                                               20

<210> SEQ ID NO 18
<211> LENGTH: 27
<212> TYPE: DNA
<213> ORGANISM: Artificial Sequence
<220> FEATURE:
<223> OTHER INFORMATION: PROBE

<400> SEQUENCE: 18
tcggctctcc gatgttatca agtagga                                       27

<210> SEQ ID NO 19
<211> LENGTH: 20
<212> TYPE: DNA
<213> ORGANISM: Artificial Sequence
<220> FEATURE:
<223> OTHER INFORMATION: PRIMER

<400> SEQUENCE: 19
cgtccmarrg gawactgatc                                               20

<210> SEQ ID NO 20
<211> LENGTH: 20
<212> TYPE: DNA
<213> ORGANISM: Artificial Sequence
<220> FEATURE:
<223> OTHER INFORMATION: PRIMER

<400> SEQUENCE: 20
gcmcagggwc ataayaatgg                                               20

<210> SEQ ID NO 21
<211> LENGTH: 30
<212> TYPE: DNA
<213> ORGANISM: Artificial Sequence
<220> FEATURE:
<223> OTHER INFORMATION: PROBE

<400> SEQUENCE: 21
tttgttactg ttgtgagata ccactcgcag                                    30

<210> SEQ ID NO 22
```

```
<211> LENGTH: 20
<212> TYPE: DNA
<213> ORGANISM: Artificial Sequence
<220> FEATURE:
<223> OTHER INFORMATION: PRIMER

<400> SEQUENCE: 22
gaagagccaa ggacaggtac                                               20

<210> SEQ ID NO 23
<211> LENGTH: 20
<212> TYPE: DNA
<213> ORGANISM: Artificial Sequence
<220> FEATURE:
<223> OTHER INFORMATION: PRIMER

<400> SEQUENCE: 23
caacttcatc cacgttcacc                                               20

<210> SEQ ID NO 24
<211> LENGTH: 24
<212> TYPE: DNA
<213> ORGANISM: Artificial Sequence
<220> FEATURE:
<223> OTHER INFORMATION: PRIMER

<400> SEQUENCE: 24
taagcaaata gatggctctg ccct                                          24
```

KIT FOR DETECTING SILENT SEXUALLY TRANSMITTED DISEASES (SSTDS) IN A URINE SAMPLE

CROSS REFERENCE TO RELATED APPLICATION

This Application is a 371 of PCT/IB2017/051265 filed on Mar. 3, 2017, which is incorporated herein by reference.

The present invention describes a Kit for simultaneously detecting pathogens that can cause silent sexually transmitted diseases (STDs) from non-invasive human urine samples, hereinafter called "Kit-U". The group of pathogens detected are: Herpes Virus type 1, Herpes Virus type 2, *Chlamydia trachomatis, Ureaplasma urealitycum, Mycoplasma hominis, Mycoplasma genitalium* and Human papillomavirus (HPV). A set of 24 sequences formed by 16 primers and 8 probes are used to carry out this detection, primers and probes that uniquely identify each one of the pathogens of said group. Sequences known in the art are used in the HPV case. The use of said sequences and the method of detecting said pathogens are herein described. Today, there are no efficient, fast, and economical techniques to simultaneously diagnose STDs from a non-invasive human biological sample.

This Kit-U is based on said sequences to perform a method starting with the extraction of the DNA present in a urine sample, amplifying said DNA through a single-reaction multiplex PCR, amplifying more than one DNA sequence from different pathogens in this case, and which includes labelling, and subsequently denaturating and hybridizing said amplified and labeled DNA on a nylon membrane in a diagnostic strip for visualizing results with specific probes complementary to sequences specific of each pathogen, which allows detecting the presence of any one of the pathogens in the urine sample, detecting the label included in the amplified DNA sequences, which results in a purple line on said membrane for visualizing results.

BACKGROUND

Sexually transmitted diseases (STDs) are caused by a set of pathogens and viruses, which cause skin lesions, pruritus, pain, and in some cases fever, among other symptoms. These pathogens have also been linked to infertility and/or spontaneous abortions. Treatments for these infections are based on the application of antibiotics, and/or antiviral medications. In this sense, the specific detection of which pathogen(s) is(are) present in a sample is a technical problem of important interest, since it defines the most appropriate treatment to be followed in each case.

Today, there is no alternative on the market for simultaneously diagnosing *Ureaplasma urealitycum, Mycoplasma hominis, Chlamydia trachomatis,* Herpes Virus, and HPV, using a single test from a single sample. In addition, the methodologies used in the art such as cell cultures, Fluorescence and Real-Time PCR are expensive, difficult to implement and maintain, have little specificity and are difficult to access by the population, health services and laboratories. On the other hand, STD treatments are expensive and patients, in most cases, are treated with antimicrobials for several weeks. A broad-spectrum antibiotic is chosen when diagnosis is non-specific, but said antibiotic may generate future resistance to an eventual STD contagion. In this way, arises the problem of having a single Kit from a single sample, which simultaneously and quickly could detect pathogens such as Herpes and *Chlamydia trachomatis* which have proven to be co-adjuvants, increasing the risk of persistence of HPV Virus and HIV-AIDS infection, because they induce an inflammatory process by increasing the irrigation of affected areas, causing epithelia microlacerations.

STDs are usually detected an identified through invasive-type samples such as blood, or cytobrush, among others, so that urine becomes a simpler and non-invasive sample to detect these infections.

The market currently offers several alternatives for the detection of pathogens causing Silent Sexually Transmitted Diseases (STDs) from urine samples. For example, commercial kits: GeneProof Herpes Simplex Virus 1 (HSV-1) PCR Kit, GeneProof Herpes Simplex Virus 2 (HSV-2) PCR Kit, GeneProof *Chlamydia trachomatis* PCR Kit, GeneProof *Ureaplasma* PCR Kit, GeneProof *Mycoplasma genitalium/hominis* PCR Kit, which make a separate and individual detection of each pathogen or bacteria or virus, from urine or blood samples. However, none of these kits describe simultaneous detection of several pathogens in the same test from a single non-invasive sample, such as urine.

WO2015034764 describes a method and kit for detecting Human papillomavirus (HPV); U.S. Pat. No. 4,937,199 describes Herpes detection method; U.S. Pat. No. 5,516,638 describes *Chlamydia trachomatis* detection method; all of these documents detect pathogens from human urine samples. These documents describe specific detection methods for each one of the pathogens of interest disclosed by the present application, using different and specific techniques for each type of pathogen (bacteria and/or virus), but the integration of all these methods within a technical macro does not allow to achieve the simultaneous identification of different pathogens. However, none of these documents describes a single method and kit to simultaneously diagnose each one of these pathogens.

The present application describes a Kit aimed at detecting pathogens that cause the most frequent silent sexually transmitted diseases in the general human population, allowing sub-grouping infected patients, which in the case of *Ureaplasma urealitycum, Mycoplasma hominis, Chlamydia trachomatis,* Herpes Virus and HPV will be able to timely access to treatment. *Chlamydia trachomatis* and Herpes Virus, are HPV co-adjuvants, therefore, patients known to be carriers of these pathogens could be more frequently followed-up to detect the pathology in early stages, preventing pre-neoplastic lesions. *Chlamydia trachomatis*, on the other hand, can affect reproductive capacity in both men and women.

In the case of HPV, the short-term clinical utility is the follow-up of patients, therapeutic decision, vaccination, and the long-term clinical utility is reduction of infertility and cervical or other HPV-associated cancer rates.

TECHNICAL PROBLEM

Currently, Silent Sexually Transmitted Diseases (STDs) diagnostic tests only relate to the detection and/or identification of a causative agent by analysis, which generally require a complex and expensive implementation in equipment; taking a period of time that can reach up to seven days during which the patient cannot receive an appropriate treatment. Thus, the rapid and economical detection of STDs is generally a frequent problem of laboratories and health services. Therefore, there is a need to develop methodologies, and sensitive kits that, at a low cost, allow multiple silent STDs to be detected simultaneously in a single non-invasive sample such as urine, allowing to apply the specific treatment according to the detected pathogen.

SUMMARY

The present invention describes a Kit for simultaneously detecting pathogens causing Silent Sexually Transmitted Diseases (STDs) from a single non-invasive human urine sample, hereinafter called "Kit-U". The group of pathogens detected are: Herpes Virus type 1, Herpes Virus type 2, *Chlamydia trachomatis, Ureaplasma urealitycum, Mycoplasma hominis, Mycoplasma genitalium*, in addition to Human papillomavirus (HPV), Kit that uses already known probe and primers. To perform this simultaneous detection, the present invention describes a set of 24 sequences formed by 16 primers and 8 probes, which distinctively identify the first 6 pathogens of the group. In the case of HPV, 3 known sequences are used. It is necessary to detect the first 6 pathogens of the group together with HPV, because the dynamic of these pathogens is synergistic. The present Kit-U uses 3 known sequences (2 primers and 1 probe) which identify a portion of the β-globin constituent gene as a control for DNA correct extraction, in order to detect the pathogens of interest. The use of the sequences and method of detection of said pathogens are herein described, method that seeks to deliver an easy, fast, and economical diagnostic tool for simultaneous detection from a single non-invasive human urine sample. The easy implementation and use of this Kit-U would allow its implementation in any diagnostic laboratory, considering that the process takes approximately 8 hours from the arrival of the sample at the laboratory until obtaining a result to report. Offering an alternative where with a single sample can simultaneously detect the presence of 7 pathogens results in a cost reduction in sample processing and analysis, which would allow to reach a larger population that could have access to a cheaper and faster alternative test, especially considering that currently each pathogen panel is separately analyzed thus increasing the cost of these tests. The pathogens detected are: Herpes Virus type 1, Herpes Virus type 2, *Chlamydia trachomatis, Ureaplasma urealitycum, Mycoplasma hominis, Mycoplasma genitalium* and additionally Human papillomavirus (HPV) for which known sequences are used.

The quick diagnosis obtained by this Kit-U allows delivering a treatment limited to the pathogen effectively affecting the patient, avoiding over-medication that could generate future resistance to a possible STD contagion.

DESCRIPTION OF THE INVENTION

Figure 1:
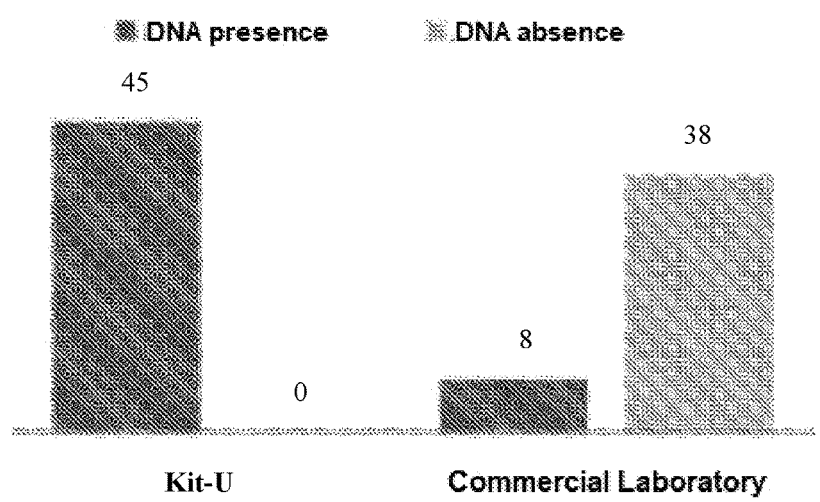
FIG. 1. Comparative graph of the Presence/Absence of DNA in urine samples. This graph shows that Kit-U detected the presence of DNA in 46 samples of the total of 46 samples tested, while the commercial laboratory kit only detected the presence of DNA in 8 samples. Using the same initial sample concentration in both cases. This shows that Kit-U sensitivity is higher than that of the commercial laboratory kit.

The present invention describes a Kit for simultaneously detecting pathogens causing Silent Sexually Transmitted Diseases (STDs) from a single non-invasive human urine sample, herein called "Kit-U". The group of pathogens of interest detected are:
Herpes Virus type 1,
Herpes Virus type 2,
*Chlamydia trachomatis,*
*Ureaplasma urealitycum,*
*Mycoplasma hominis,*
*Mycoplasma genitalium*, and
Human papillomavirus (HPV).

The present invention describes a set of 24 sequences, wherein SEQ ID NOs: 1 to 18 are specifically designed for the detection of the first 6 pathogens of the group of pathogens of interest using 2 primers and 1 probe for each pathogen. Three already known sequences (2 primers, 1 probe) are used for HPV. Additionally, the present Kit-U requires the detection of the β-globin gene (internal control for DNA quality and amplification), for which another 3 known in the art sequences are used. This Kit-U allows to perform a detection method based on Multiplex PCR amplification of genome region sequences of different pathogens. The PCR product is hybridized on a diagnostic strip formed by a nylon membrane containing specific probes for different pathogens.

The primers used in the Multiplex PCR step are previously labeled at their 5' end with a digoxigenin molecule, which is used to detect the pathogen presence. Probes have a 5' end modification with an Amino Modifier C6, (AmMC6) allowing the probe to adhere to the nylon membrane in the diagnostic strip.

If the genome of any of the pathogens of interest to be detected is coupled to its complementary probe, it exposes the Digoxigenin molecule in one of the primers now located in the amplified DNA. This Digoxigenin molecule is detected through a reaction with anti-Digoxigenin antibody, this antibody is conjugated to alkaline phosphatase for its visualization with compound NB T/BCIP (5-bromo-4-chloro-3-indolyl-phosphate/nitro blue tetrazolium), which forms a purple precipitate on the membrane at the site of the probe that reacted with the pathogen DNA present in the sample.

Hybridization between the pathogen DNA present in the urine sample and the specific probe is visualized by a color precipitate. The diagnostic strip includes a probe for the β-globin gene already known in the art, as amplification internal control. Detection zones are located in the diagnostic strip according to a spatial pattern (FIG. 4), established so that the diagnostic strip is compared with said pattern to determine the presence or absence of each specific pathogen.

More specifically, the present application describes a diagnostic kit to simultaneously detect at least 7 silent Sexually Transmitted Diseases (STDs), which comprises a diagnostic strip, comprising detection zones with at least 8 probes of SEQ ID NOs: 3, 6, 9, 12, 15, 18, 21, 24; at least 14 primers of SEQ ID NOs: 1, 2, 4, 5, 7, 8, 10, 11, 13, 14, 16, 17, 19, 20, 22, 23; instruction manual.

The present specification also describes SEQ ID NOs: 1 to 18, each one separately, and sequences having at least 90% similarity thereof.

The present application also describes a set of 24 nucleotide sequences described in detail in Table 1, the first 18 nucleotide sequences, SEQ ID NOs: 1 to 18, were designed specifically for this invention. Sequences 19 to 21 are known in the art for HPV detection, and sequences 22 to 24 are known in the art for β-globin detection. The nucleotide sequences of 2 primers and 1 probe, respectively, for each target pathogen to be detected are also described. The primers are useful to carry out an amplification of specific segments by Multiplex PCR amplification step, while the probe is useful to perform the detection of said amplified segments.

Probes having SEQ ID NOs: 3, 6, 9, 12, 15, 18, 21, 24 have a modification at the 5' end (Amino Modifier C6, AmMC6) which allows their adhesion to the nylon membrane in the diagnostic strip.

The present application describes the use of SEQ ID NOs: 1 to 24, for the preparation of a diagnostic kit comprising the same, useful for the detection of pathogens causing sexually transmitted diseases. Another embodiment of the present application is the use of the kit to detect at least pathogens of group: Herpes Virus type 1, Herpes Virus type 2, *Chlamydia trachomatis, Ureaplasma urealitycum, Mycoplasma hominis, Mycoplasma genitalium*, and Human papillomavirus (HPV).

Sequences SEQ ID NOs: 1, 2, 3 are used for the detection of Human Herpes virus 1.

Sequences SEQ ID NOs: 4, 5, 6 are used for the detection of Human Herpes virus 2.

Sequences SEQ ID NOs: 7, 8, 9 are used for the detection of *Chlamydia trachomatis*.

Sequences SEQ ID NOs: 10, 11, 12 are used for the detection of *Ureaplasma urealyticum*.

TABLE 1

| PATÓGEN | Target | | Sequence (5'3') | SEQ ID NO |
|---|---|---|---|---|
| Human herpes virus 1 | DNA polymerase gene | PRIMER PRIMER PROBE | TGGCCAAGCTGACGGACATTT 5DigN/GAGAGCTTGATCTTGTCGGTT /5AmMC6/TAAAGGTGAACGGCATGGTGAGCA | 1 2 3 |
| Human herpes virus 2 | Virion glycoprotein I and virion glycoprotein E gene | PRIMER PRIMER PROBE | TGTTTCTGGGCAGCTGTATC 5DigN/CTATCGACGTTAGGGAAGGCAT /5AmMC6/CATAGATGCCAGCGCCGATACAGG | 4 5 6 |
| *Chlamydia trachomatis* | Major outer membrane protein Gene | PRIMER PRIMER PROBE | TCAAGGAGTGGAGTGTCTGCGTA 5DigN/TGTCGCTCCGA TGCAGATGTTT /5AmMC6/ATAGGGAGTGTTTCTCGCCAAGCT | 7 8 9 |
| *Ureaplasma urealyticum* | 16S RNA ribosomal gene | PRIMER PRIMER PROBE | GCAGGCGGGTTTGTAAGTTTGGTA 5DigN/AGCCTAAGCGTCAGTGATAGTCCA /5AmMC6/ATAGGAAGAACACCGGTGGCGAA | 10 11 12 |
| *Mycoplasma hominis* | 16S RNA ribosomal gene | PRIMER PRIMER PROBE | TGGAGAATCACTGACGCAGCTAAC 5DigN/TGCGAAGGATGTCAAGAGTGGGTA /5AmMC6/CCGCCTGAGTAGTATGCTCGCAAG | 13 14 15 |
| *Mycoplasma genitalium* | 30S ribosomal protein S3 | PRIMER PRIMER PROBE | CGCAACGCTCAGGTGTCTAATGT 5DigN/AGAGCTTGG CGCATTGCTGA /5AmMC6/TCGGCTCTCCGATGTTATCAAGTAGGA | 16 17 18 |
| HPV | Virus region L1 | PRIMER PRIMER PROBE | CGTCCMARRGGAWACTGATC 5DigN/GCMCAGGGWCATAAYAATGG /5AmMC6/TTTGTTACTGTTGTGAGATACCACTCGCAG | 19 20 21 |
| β-globine | Constitutive gene | PRIMER PRIMER PRIMER | 5DigN/GAAGAGCCAAGGACAGGTAC CAACTTCATCCACGTTCACC /5AmMC6/TAAGCAAATAGATGGCTCTGCCCT | 22 23 24 |

The present application also describes a set consisting of 24 sequences that have at least 90% similarity to the sequences of the set described in Table 1.

Sequences 19 to 24 are known in the art. They are herein described since HPV and β-globin detection is required as a control, together with the detection of the rest of the pathogens of the group: Herpes Virus type 1, Herpes Virus type 2, *Chlamydia trachomatis, Ureaplasma urealitycum, Mycoplasma hominis, Mycoplasma genitalium*.

Primers having SEQ ID NOs: 2, 5, 8, 11, 14, 17, 20 and 22 are labeled at their 5' end with Digoxigenin molecule. This marker molecule allows subsequently detect the hybridized sequences, thus identifying the corresponding pathogen.

Sequences SEQ ID NOs: 13, 14, 15 are used for the detection of *Mycoplasma hominis*.

Sequences SEQ ID NOs: 16, 17, 18 are used for the detection of *Mycoplasma genitalium*.

Sequences SEQ ID NOs: 19, 20, 21, known in the art, are used for the detection of Human papillomavirus (HPV).

Sequences SEQ ID NOs: 22, 23, 24, known in the art, are used for the detection of β-globin gene, a constitutive gene that is used to control the correct extraction of DNA from the sample.

The present application also describes a method for simultaneously detecting at least 7 Silent Sexually Transmitted Diseases (STDs), which comprises the steps of:

i) extracting DNA from a body fluid sample by cell lysis, and centrifuging to obtain a pellet containing DNA samples to be amplified; wherein body fluids are selected from urine, blood, saliva, urethral secretion, seminal fluid, vaginal secretion;
ii) amplifying by Multiplex PCR using the primers described in SEQ ID NOs: 1, 2, 4, 5, 7, 8, 10, 11, 13, 14, 16, 17, 19, 20, 22, 23; copies of DNA segments complementary to said primers are amplified;
iii) hybridizing the amplified DNA in step ii), using the probes described in SEQ ID NOs: 3, 6, 9, 12, 15, 18, 21, 24, by a hybridization reaction between the copies obtained in amplification of step ii) using said probes;
iv) detecting the presence or absence of pathogens of interest on a nylon membrane comprising the probes of SEQ ID NOs: 3, 6, 9, 12, 15, 18, 21, 24, spatially arranged according to a spatial pattern previously determined.

Example

Step 0:
Preparation of urine sample for DNA extraction, transport medium removal.

The sample was transferred to a 15 mL falcon tube, until a pellet from the total urine sample was obtained.

It was centrifuged at 4,000 rpm for 15 min at room temperature (RT) at 20 to 22° C. The supernatant was removed, taking care not to detach the pellet.

1. 300 µL of Saline Phosphate Buffer (PBS) or Dubelcco Saline Phosphate Buffer (DPBS) was added. Between 300 and 600 µL of PBS can be added, depending on the pellet size.
2. The sample was then divided into two 1.5 mL Eppendorf tubes.
3. It was centrifuged at 12,000 rpm, for 5 min at RT.
4. The supernatant was removed carefully.
5. 500 µL of Lysis Solution was added.
6. It was left 12 hours at RT, and DNA extraction was continued.

Step i
DNA Extraction

After removing the transport medium and adding 500 mL of lysis buffer to begin cell lysis, an extraction procedure was performed according to the steps described below:

Note: Samples must have a minimum volume of 500 mL at the beginning of the extraction process.

1. Adding 250 mL of 100% ethanol. Mixing vigorously in vortex.
2. The extraction column was inserted into the 2 mL collection tubes.
3. The total of the sample from step 1 was transferred in the extraction column including any precipitate that may have been formed.
4. Centrifuging at maximum speed (>10,000×g) for 1 minute.
5. The filtrate was removed and the collection tube was reused.
6. 500 mL of HBC Buffer (Wash Solution 1) was added.
7. HBC Buffer was diluted with isopropanol before use
8. Centrifuging at maximum speed for 30 seconds.
9. Filtrate and collection tube were removed.
10. The extraction column was inserted into a new 2 mL collection tube.
11. 700 mL of DNA Wash Buffer (Wash Solution 2) was added. DNA Wash Buffer was diluted with 100% ethanol before use.
12. Centrifuging at maximum speed for 30 seconds.
13. Filtrate was removed and the collection tube was reused.
14. Steps 10-12 were repeated for a second wash step with DNA Wash Buffer (Wash Solution 2).
15. The empty extraction column was centrifuged at maximum speed for 2 minutes to dry the column.
16. 100 mL of Elution Buffer (Elution Solution) preheated to 70° C. was added.
17. It was left at room temperature for 2 minutes.
18. It was centrifuged at 15,000 g for 1 minute.

Stage ii.
Amplification of the extracted DNA.

This step was performed to increase the number of genome copies of pathogens from the group of interest to be detected. This is achieved with the use of primers of SEQ ID NOs: 1, 2, 4, 5, 7, 8, 10, 11, 13, 14, 16, 17, 19, 20, 23 and 24 described in Table 1. Which are labeled at their 5' end with a Digoxigenin molecule that is reacted in the next step (hybridization).

These primers are contained in the PCR Mix.

1. 20 µL of PCR Mix was distributed in each PCR tube.
2. Adding:
   5 µL of sample to each tube
   5 µL Positive control
   5 µL Blank Control
3. Tubes were capped. Vortex for 3 sec. watching that there were no bubbles left.
4. Tubes were placed in a thermal cycler with the following program:
   Denaturation: 94° C./3 min.
   34 cycles: 94° C./30 sec, 56° C./30 sec, 72° C./30 sec.
   Extension: 72° C./3 min.

Step iii.
Amplified DNA Hybridization.

In this step, the amplified genome copies of step ii were reacted with the probes of SEQ ID NO 3, 6, 9, 12, 15, 18, 21 and 24 described in Table 1.

Method:
Hybridization
(Method time: 3 h 30 min)
Important: Before Starting the Method:
a. Hybridization solution, Wash Solution 3, Wash Solution 4 and Wash Solution 5 were heated and maintained at 42° C. until used.

A. PCR Product Denaturation:
1. 85 µL of Hybridization Solution was added to a 0.5 mL tube and then 15 µL of the PCR product was added. The tube was well capped.
2. Denaturing at 96° C. for 10 min. The tubes of the Thermocycler or thermal block were removed and immediately cooled on ice for 5 min.

Extreme care was taken on maintaining the tubes closed to prevent amplicon contamination; especially when working with 0.2 mL tubes.

3. Centrifuging the tubes at 10,000×g for 10 sec before opening to avoid contamination.

B. Diagnostic Strip Hydration

While the tubes were cooled on ice (step 2, above), 200 µL of Hybridization Solution was added in an 8-channel tray, the diagnostic strips were added and hydrated at room temperature for 5 min. The diagnostic strips were removed with a tweezer from the tube containing the same.

C. Hybridization of PCR Products on Diagnostic Strips
1. Denaturated PCR products were added (100 µL) on each diagnostic strip, and incubated at 42° C. for 60 min gently shaking, avoiding bubbles.
2. Hybridization Solution was removed with a sterile plastic Pasteur pipette
3. 1 mL of Wash Solution 3 was added. Incubated at 42° C. for 10 min with stirring. Step 3 was repeated.
4. Wash Solution 3 was removed with a sterile plastic Pasteur pipette and 1 mL of Wash Solution 4 was added. It was incubated at 42° C. for 2 min with shaking.
5. Conjugate Solution was prepared by adding 1.3 µL of Conjugate to the Conjugate Solution. It was mixed inverting (NO Vortex).
6. Wash Solution 4 was removed with a sterile plastic Pasteur pipette and 0.5 mL of freshly prepared Conjugate Solution was added. It was incubated at 42° C. for 30 min with shaking. Conjugate Solution was removed.
7. 1 mL of Wash Solution 5 was added. Incubated at 42° C. for 5 min with shaking. This step was repeated.
8. Wash Solution 5 was removed.

D. Development of the Diagnostic Strip
1. 0.5 mL of Substrate Solution was added. It was incubated at 42° C. for 30 min in darkness without shaking.
2. Reaction was stopped by adding approximately 1 mL of distilled water with a pipette. This step was repeated at least twice.
3. Water was removed by inversion taking care not to sweep along the diagnostic strips. 2 mL of distilled water was added, left to stand for at least 30 min.
4. The diagnostic strips were removed with tweezers and placed on a paper sheet to dry. Once dried they were covered with a scotch tape to store them. Optional: can be digitized.
5. The results are obtained immediately. The diagnostic strip was placed parallel to the pattern (FIG. 4) included in the kit.

Step iv
Results and Interpretation of the Diagnostic Strip

The diagnostic strip contains specific probes to detect pathogens: Herpes Virus type 1, Herpes Virus type 2, *Chlamydia trachomatis, Ureaplasma urealitycum, Mycoplasma hominis, Mycoplasma genitalium* and Human papillomavirus (HPV). These probes are immobilized in the diagnostic strip, allowing a simple reading from visualizing a mark in a specific spatial zone in the strip.

Controls
POSITIVE: there must be presence of bands for all the pathogens contained in the kit, including β-globin band.
BLANK: absence of bands.

This example was performed twice, a first time using the primers and probes described in Table 1 of this Kit-U, and a second time using the primers and probes contained in a commercial laboratory kit. It allowed to obtain comparative results (FIGS. 1, 2, 3) regarding he detection sensitivity obtained with the sequences described in the present application compared to the sensitivity obtained using the sequences of a commercial laboratory kit.

Figure 4:
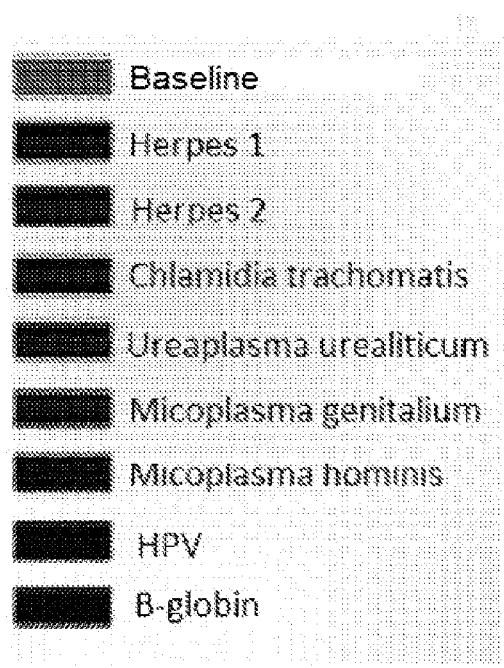
FIG. 4. This figure shows the spatial pattern showing the location of the detection probes for each pathogen. The detection strips are located parallel to this pattern to identify which pathogens are present in the sample.

The results can be read by facing each diagnostic strip to the pattern containing the ordered probes shown in FIG. 4, trying to match the baseline to ensure the correct interpretation of the results.

A comparative analysis versus the Commercial Laboratory Kit was carried out to validate this Kit-U, samples were taken from 47 patients who donated two urine samples each. Both samples were taken at the same time.

FIG. 1 shows a comparison of sensitivity between KIT-U vs. Commercial Laboratory Kit. Using the Kit-U it was possible to obtain enough DNA from 100% of the urine samples to obtain a result. In contrast, the analysis performed using the commercial laboratory kit did not detect the presence of DNA in 82.6% (n=38) of the samples.

Figure 2:
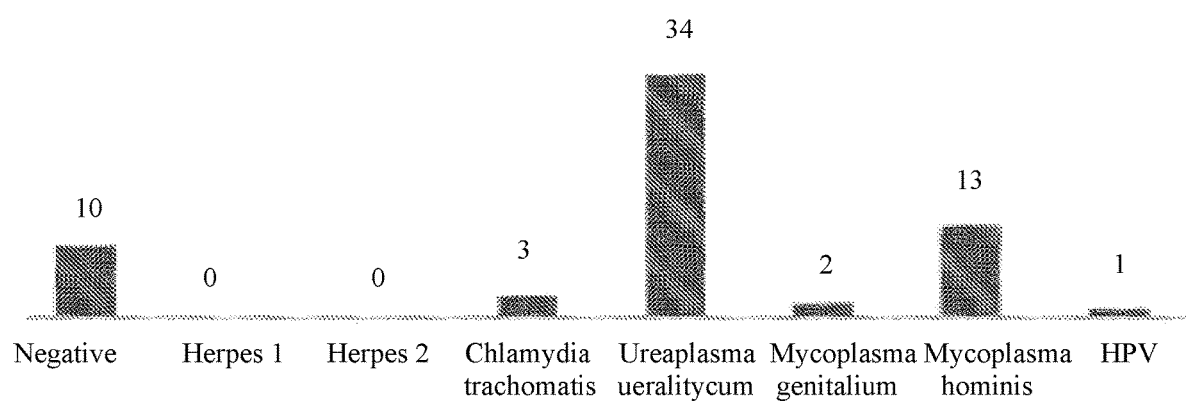
FIG. 2. Graph showing the distribution of results obtained when analyzing the samples with Kit-U. Distribution of m.o. detected by Kit-U. This graph shows the distribution of the detections made using Kit-U, finding 34 detections for *Ureaplasma urealiticum*, 13 for *Mycoplasma hominis*, 3 *Chlamidia trachomatis*, 2 *Mycoplasma genitalium*, 1 HPV, and 10 negative samples.
Figure 3:
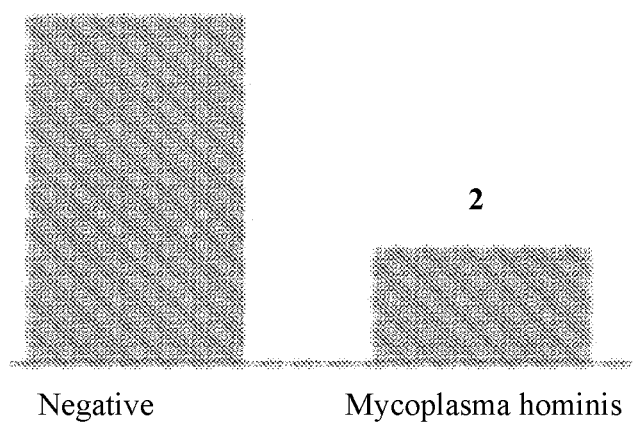
FIG. 3. Graph showing the distribution of results obtained when analyzing the samples by Commercial Laboratory. Distribution of m.o. detected by Commercial Laboratory. This graph shows the distribution of the detections made with the Commercial Laboratory Kit, finding that of the total of 8 samples detected by DNA, only 2 detections identify *Mycoplasma hominis*, while the remaining 6 samples were not identified.

FIG. 2 shows the pathogens detected using the Kit-U. It is observed that Kit-U was able to detect the presence of at least one pathogen in 78.2% (n=36) of the analyzed samples, with only 21.8% (n=10) of negative cases.

In contrast, when using the commercial laboratory kit—see results in FIG. 3A—from the total samples (n=8) where DNA was detected, 75% (n=6) were negative for the pathogens evaluated and only 25% (n=2) were positive for *Mycoplasma hominis*.

This shows that the primers and probes described in SEQ ID NOs: 1 to 18 comprised by the Kit-U, provide improved sensitivity compared to the primers and probes of the Commercial Laboratory Kit.

It is important to mention that these sequences of primers and probes designed for this Kit-U, SEQ ID NOs: 1 to 18, together with the additional sequences 19 to 24 known from the art and using the detection method, can be used with any biological sample from which amplifiable DNA can be obtained, preferably fluids, such as blood, saliva, urethral secretion, seminal fluid, vaginal secretion.

The invention claimed is:

1. A diagnostic kit for simultaneously detecting at least 7 silent sexually transmitted diseases (STDs), comprising:
   a diagnostic strip, comprising detection zones with at least 8 probes of SEQ ID NOs: 3, 6, 9, 12, 15, 18, 21, 24;
   at least 14 primers of SEQ ID NOs: 1, 2, 4, 5, 7, 8, 10, 1 1, 13, 14, 16, 17, 19, 20, 22, 23;
   instruction manual.

2. A method for simultaneously detecting at least 7 silent sexually transmitted diseases (STDs), comprising the steps of:
   i. extracting DNA from a body fluid sample by cell lysis, and centrifuging to obtain a pellet containing DNA samples to be amplified;
   ii. amplifying by Multiplex PCR, using the primers comprising SEQ ID NOs: 1, 2, 4, 5, 7, 8, 10, 1 1, 13, 14, 16, 17, 19, 20, 22, and 23;
   iii. hybridizing the amplified DNA in step ii), using the probes comprising SEQ ID NOs: 3, 6, 9, 12, 15, 18, 21, and 24;
   iv. detecting the presence or absence of the pathogens of interest in a nylon strip comprising the probes of SEQ ID NOs: 3, 6, 9, 12, 15, 18, 21, 24.

3. The method of claim 2 wherein step i), body fluid samples are selected from urine, blood, saliva, urethral secretion, seminal fluid, vaginal secretion.

4. The method of claim 2, wherein in step iv) the pathogen detected is at least one of the pathogens selected from the group consisting of Herpes Virus type 1, Herpes Virus type 2, *Chlamydia trachomatis, Ureaplasma urealitycum, Mycoplasma hominis, Mycoplasma genitalium*, and Human papillomavirus (HPV).

5. A set of nucleic acid molecules for simultaneously detecting at least 7 silent sexually transmitted diseases (STDs), comprising the following sequences:

| Sequence (5'3') | SEQ ID NO: |
|---|---|
| TGGCCAAGCTGACGGACATTT | 1 |
| 5DigN/GAGAGCTTGATCTTGTCGGTT | 2 |
| /5AmMC6/TAAAGGTGAACGGCATGGTGAGCA | 3 |
| TGTTTCTGGGCAGCTGTATC | 4 |
| 5DigN/CTATCGACGTTAGGGAAGGCAT | 5 |
| /5AmM6/CATAGATGCCAGCGCCGATACAGG | 6 |
| TCAAGGAGTGGAGTGTCTGCGTA | 7 |
| 5DigN/TGTCGCTCCGATGCAGATGTTT | 8 |
| /5AmMC6/ATAGGGAGTGTTTCTCGCCAAGCT | 9 |
| GCAGGCGGGTTTGTAAGTTTGGTA | 10 |
| 5DigN/AGCCTAAGCGTCAGTGATAGTCCA | 11 |
| /5AmMC6/ATAGGAAGAACACCGGTGGCGAA | 12 |
| TGGAGAATCACTGACGCAGCTAAC | 13 |
| 5DigN/TGCGAAGGATGTCAAGAGTGGGTA | 14 |
| /5AmMC6/CCGCCTGAGTAGTATGCTCGCAAG | 15 |
| CGCAACGCTCAGGTGTCTAATGT | 16 |
| 5DigN/AGAGCTTGGCGCATTGCTGA | 17 |
| /5AmMC6/TCGGCTCTCCGATGTTATCAAGTAGGA | 18 |
| CGTCCMARRGGAWACTGATC | 19 |
| 5DigN/GCMCAGGGWCATAAYAATGG | 20 |

-continued

| Sequence (5'3') | SEQ ID NO: |
|---|---|
| /5AmMC6/TTTGTTACTGTTGTGAGAT ACCACTCGCAG | 21 |
| 5DigN/GAAGAGCCAAGGACAGGTAC | 22 |
| CAACTTCATCCACGTTCACC | 23 |
| /5AmMC6/TAAGCAAATAGATGGCTCTGCCCT | 24; | and
 wherein the modification AmMC6 at the 5' end of SEQ ID NOs: 3, 6, 9, 12, 15, 18, 21 and 24 adhere to a diagnostic strip.

* * * * *